(12) United States Patent
Heyman

(10) Patent No.: US 12,193,920 B2
(45) Date of Patent: Jan. 14, 2025

(54) ADJUSTABLE PERSONAL HYGIENE ARTICLE

(71) Applicant: Dermasteel, Ltd., Gahanna, OH (US)

(72) Inventor: Ian A. Heyman, Pataskala, OH (US)

(73) Assignee: Dermasteel, Ltd., Reynoldsburg, OH (US)

( * ) Notice: Subject to any disclaimer, the term of this patent is extended or adjusted under 35 U.S.C. 154(b) by 1168 days.

(21) Appl. No.: 16/791,527

(22) Filed: Feb. 14, 2020

(65) Prior Publication Data

US 2020/0261280 A1   Aug. 20, 2020

Related U.S. Application Data

(60) Provisional application No. 62/805,511, filed on Feb. 14, 2019.

(51) Int. Cl.
| | | |
|---|---|---|
| *A61F 13/471* | (2006.01) | |
| *A61F 13/49* | (2006.01) | |
| *A61F 13/537* | (2006.01) | |
| *A61F 13/539* | (2006.01) | |
| *A61F 13/76* | (2006.01) | |

(52) U.S. Cl.
CPC ...... *A61F 13/471* (2013.01); *A61F 13/49014* (2013.01); *A61F 13/4906* (2013.01); *A61F 13/53708* (2013.01); *A61F 13/76* (2013.01); *A61F 2013/53983* (2013.01)

(58) Field of Classification Search
None
See application file for complete search history.

(56) References Cited

U.S. PATENT DOCUMENTS

| | | | | |
|---|---|---|---|---|
| 4,601,716 A | * | 7/1986 | Smith | A61F 5/453 604/351 |
| 4,728,326 A | * | 3/1988 | Gilles | A61F 13/49004 604/391 |
| 4,798,603 A | * | 1/1989 | Meyer | A61F 13/512 604/383 |

(Continued)

FOREIGN PATENT DOCUMENTS

| | | |
|---|---|---|
| EP | 3923887 A1 | 12/2021 |
| JP | 2004298457 A | 10/2004 |

(Continued)

OTHER PUBLICATIONS

Japanese Office Action dated Aug. 2, 2022 (with translation) (7 pages).

(Continued)

*Primary Examiner* — Michele Kidwell
(74) *Attorney, Agent, or Firm* — Taft Stettinius & Hollister LLP; Thomas E. Bejin; John Wray Carpenter

(57) ABSTRACT

A hygienic article structured to inhibit soiling of clothing from intermittent or sporadic leakage of urine from a penis over time is provided. The hygienic article provides secure and dynamically variable fit, unobtrusive appearance, and airflow to the skin. The hygienic article according to this disclosure may be as little as one eighth of the surface area of conventional male incontinence guard or shield products, and as little as one quarter of the size of other male incontinence guard products used only over a penis.

18 Claims, 6 Drawing Sheets

(56) References Cited

U.S. PATENT DOCUMENTS

| | | | | |
|---|---|---|---|---|
| 4,846,823 | A | * | 7/1989 | Enloe ................ A61F 13/49413 604/385.28 |
| 4,964,860 | A | * | 10/1990 | Gipson ................ A61F 5/4401 604/391 |
| 5,135,522 | A | * | 8/1992 | Fahrenkrug ............. A61F 13/64 604/401 |
| 5,409,476 | A | * | 4/1995 | Coates ................ A61F 13/622 604/391 |
| 5,607,416 | A | * | 3/1997 | Yamamoto ............. A61F 13/64 604/397 |
| 5,814,037 | A | | 9/1998 | Coates |
| 5,906,604 | A | * | 5/1999 | Ronnberg ............... A61F 13/64 604/386 |
| 6,306,121 | B1 | * | 10/2001 | Damaghi .......... A61F 13/49019 604/385.03 |
| 6,336,922 | B1 | | 1/2002 | VanGompel et al. |
| 6,371,950 | B1 | * | 4/2002 | Roslansky .......... A61F 13/4915 604/385.27 |
| 6,402,729 | B1 | * | 6/2002 | Boberg ............ A61F 13/49413 604/385.27 |
| 6,652,499 | B1 | * | 11/2003 | Edgren ............... A61F 13/5323 604/385.24 |
| 8,568,376 | B2 | * | 10/2013 | Delattre ................ A61F 13/471 604/385.01 |
| 8,961,482 | B2 | | 2/2015 | Heyman |
| 8,986,271 | B1 | * | 3/2015 | Horne .................... A61F 5/4408 604/385.09 |
| 9,539,151 | B2 | * | 1/2017 | Vartiainen ........... A61F 13/4915 |
| 2003/0158534 | A1 | * | 8/2003 | Niki ...................... A61F 13/471 604/385.19 |
| 2006/0167433 | A1 | * | 7/2006 | D'Alcini ................. A61F 13/64 604/392 |
| 2006/0282055 | A1 | | 12/2006 | Shiomi et al. |
| 2011/0184372 | A1 | * | 7/2011 | Esping Ostlin ... A61F 13/49012 604/392 |
| 2015/0209194 | A1 | | 7/2015 | Heyman |
| 2019/0021915 | A1 | * | 1/2019 | Honcoop .......... A61F 13/49007 |
| 2020/0261280 | A1 | | 8/2020 | Heyman |

FOREIGN PATENT DOCUMENTS

| | | |
|---|---|---|
| JP | 2007167210 A | 7/2007 |
| JP | 2022520123 A | 3/2022 |
| WO | 9848753 A1 | 11/1998 |
| WO | 2020168204 A1 | 8/2020 |

OTHER PUBLICATIONS

Extended European Search Report with Supplementary European Search Report issued by the EPO on Oct. 7, 2022 relating to Application No. PCT/US2020/018307 (7 pages).

Canadian Office Action dated Nov. 21, 2022 issued by Canadian Intellectual Property Office regarding Canadia Patent Application No. 3,130,313 (3 pages).

International Search Report and Written Opinion for PCT/US2020/018307 mailed Jun. 17, 2020.

* cited by examiner

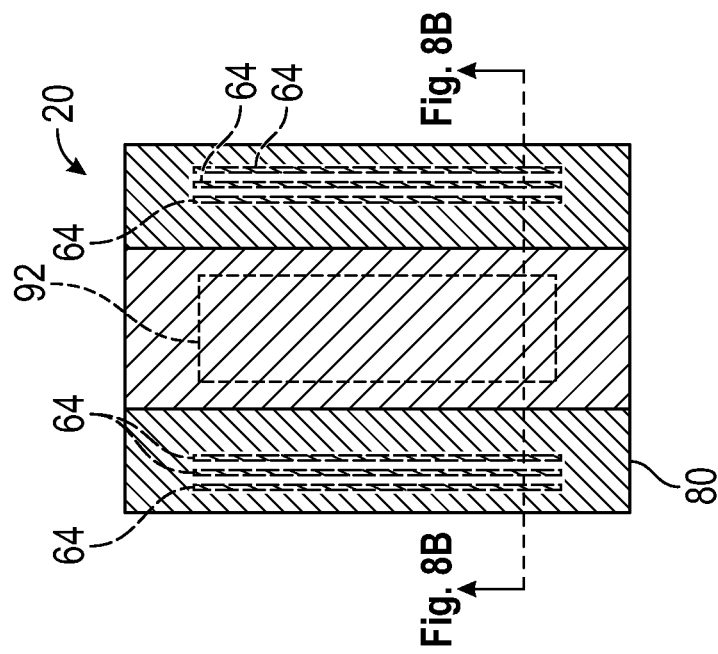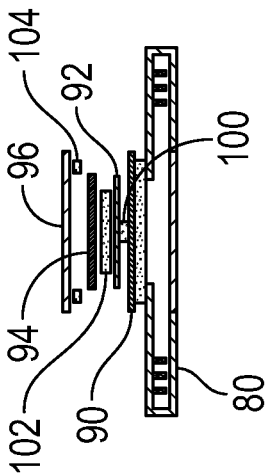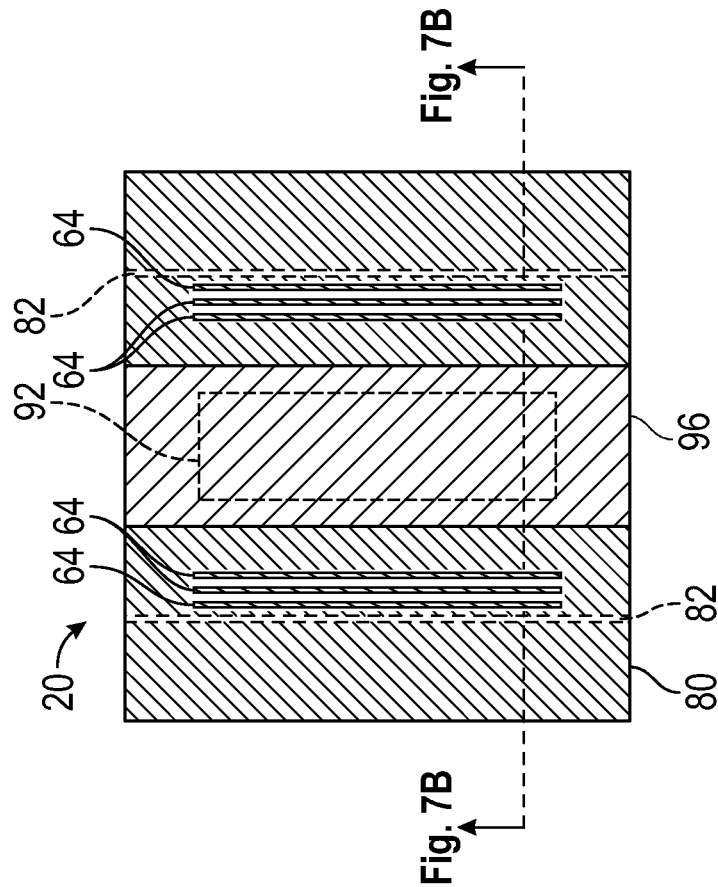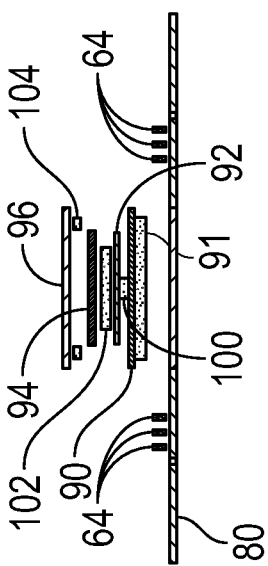

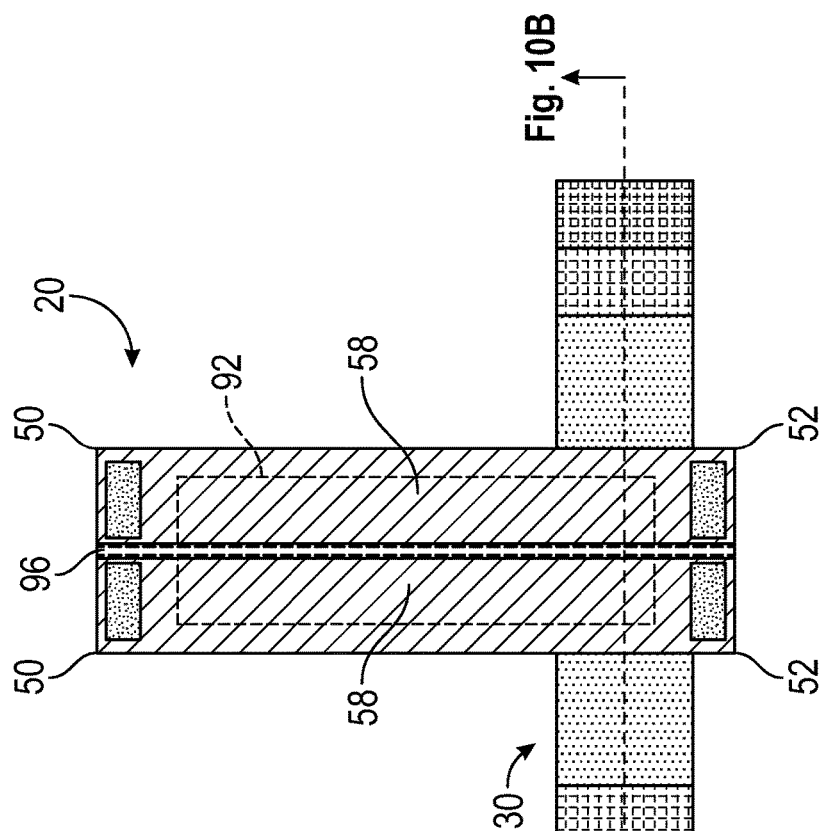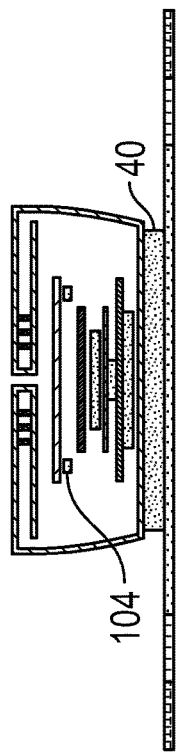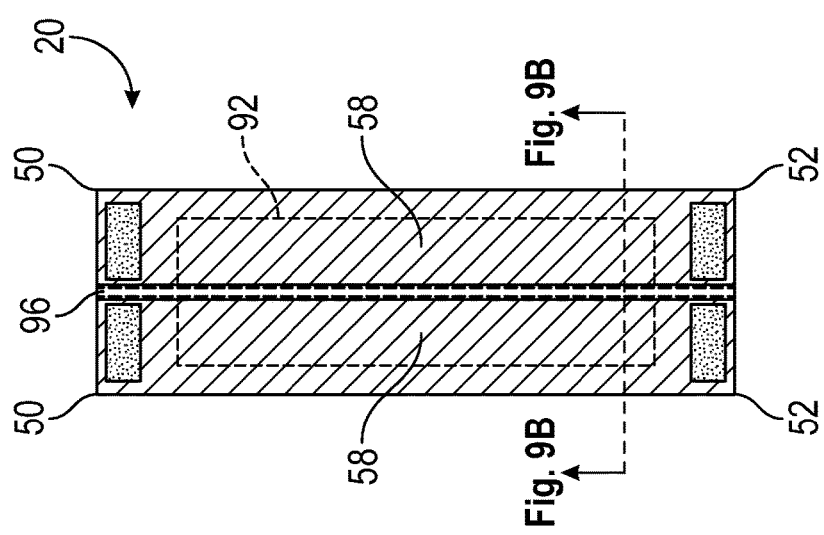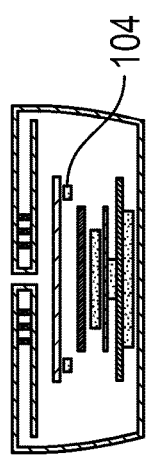

ADJUSTABLE PERSONAL HYGIENE ARTICLE

CROSS-REFERENCE TO RELATED APPLICATIONS

This patent application claims priority to, and all the benefits of, U.S. Provisional Patent Application No. 62/805,511 filed on Feb. 14, 2019, which is herein incorporated by reference in its entirety.

BACKGROUND

This present disclosure is related to a hygienic article for a male anatomy.

Incontinence can arise for many reasons and at any age. Physical trauma and any number of medical conditions can give rise to incontinence. Incontinence can also be a product of age, such as when a man's prostate becomes enlarged, surgery effects the nerves serving the bladder, or the man develops Alzheimer's disease or dementia. Incontinence may present, e.g., by the sporadic or continual trickling of urine from the penis or may result in spontaneous release of the entire contents of the bladder.

As disclosed in U.S. Pat. No. 8,961,482, a hygienic article for a male may take the form of a tube having an open end adapted to receive a limp penis and a closed second end, the tube including an absorbent material extending at least within the second end of the tube and being adapted to absorb fluids.

SUMMARY

The present disclosure provides a hygienic article for a male configured to fit and to secure to a wide range of sizes and configurations of a male penis and to adjust to variations in size and shape of a male penis during use, while conforming to the overall anatomical configuration of a user to be, e.g., practically indistinguishable under a user's clothing.

The article according to the principles of the present disclosure includes elasticized side-panels which mechanically couple distal ends of a main chassis of the article to define a pouch in the article. The elasticized side-panels are configured, in some embodiments, with a varying overall elasticity between proximal and distal attachment points of the elasticized panels to the chassis. For example, elastic threads in the elasticized side-panels may vary in size, amount, and elasticity. The variations in the elastic threads may be configured, e.g., to provide a center portion of the elasticized side-panels between the proximal and distal ends with relatively greater elasticity and, thus, relatively relaxed elasticity at the proximal and distal attachment points of the side-panels to the chassis. According to the principles of the present disclosure, the structure of the elasticized side-panels and assembly thereof as a part of the article provides a desired lateral compression towards securing the article to a user while further providing self-adjustment to accommodate and conform to localized variation in anatomical configuration, e.g. a changing size and shape of a male penis of a user during use of the article.

The hygienic article further secures to a user at the penis with a fastening component. A fastening component according to the principles of the present disclosure may be in the form of one of a strap, beading, band, strip, clamps, and belt, by way of non-limiting examples. In an example with the fastening component with a form such as a strap, the strap is configured with ends emanating from a posterior portion of the chassis of the article and includes hook material portions to engage a landing zone on the exterior of the chassis of the article, the landing zone including one or more materials varying from the chassis to provide secure attachment to the fastening strap. The strap also includes an additional landing zone on the strap itself to allow for the strap to secure to itself in an overlapping configuration. The fastening strap further includes elastic material to provide additional flexibility, with one or both of lateral and longitudinal stretch capabilities, in performance and adjustment.

BRIEF DESCRIPTION OF THE DRAWINGS

FIGS. 7A-B are top and exploded cross-sectional schematic views of a partially assembled hygienic article according to the principles of the present disclosure;

FIGS. 8A-B are top and exploded cross-sectional schematic views of a further partially assembled hygienic article;

FIGS. 9A-B are top and exploded cross-sectional schematic views of a yet further partially assembled hygienic article; and FIGS. 10A-B are top and exploded cross-sectional schematic views of an assembled hygienic article in an unfolded, stretched configuration.

DETAILED DESCRIPTION

A hygienic article according to the principles of the present disclosure is structured to inhibit soiling of clothing from intermittent or sporadic leakage of urine from a penis over time by containing and absorbing the leakage—while providing secure and dynamically variable fit, unobtrusive appearance, preventing pooling of liquid against the skin, providing airflow to the skin. With a minimized footprint, an article according to this disclosure thereby minimizes exposure of anatomy to pooling of fluid. In some embodiments, an article according to this disclosure is as little as one eighth of the surface area of conventional male incontinence guard or shield products, and as little as one quarter of the size of other male incontinence guard products used only over a penis. The size and anatomically conforming characteristics of an article according to this disclosure result in no substantial impact on the appearance of a clothed user.

A hygienic article according to this disclosure is targeted to contain leakage from the male anatomy over time, such as, by way of example only, stress or urge leakage or post-voiding incontinence, as opposed to substantial or complete emptying of the bladder in a single event or short amount of time. To provide capacity for numerous such events over time, all while minimizing footprint, an article according to this disclosure employs a relatively high density absorbent component in a structure which directs fluid away from the skin to the absorbent core. This structure of the present disclosure includes the securing of the chassis of the article while providing variable elasticity in side panels thereof, by which the article conforms and maintains the path to the absorbent core as the size and position of the male anatomy changes during use. The fluid and absorbent core are contained between a water barrier back sheet and a one-way moisture barrier (acquisition distribution layer). The article can contain sporadic, relative small amounts of liquid to accommodate the absorption rate of a high density material, with the high density absorbing material in turn providing capacity to absorb numerous leakages.

Figure 1A:
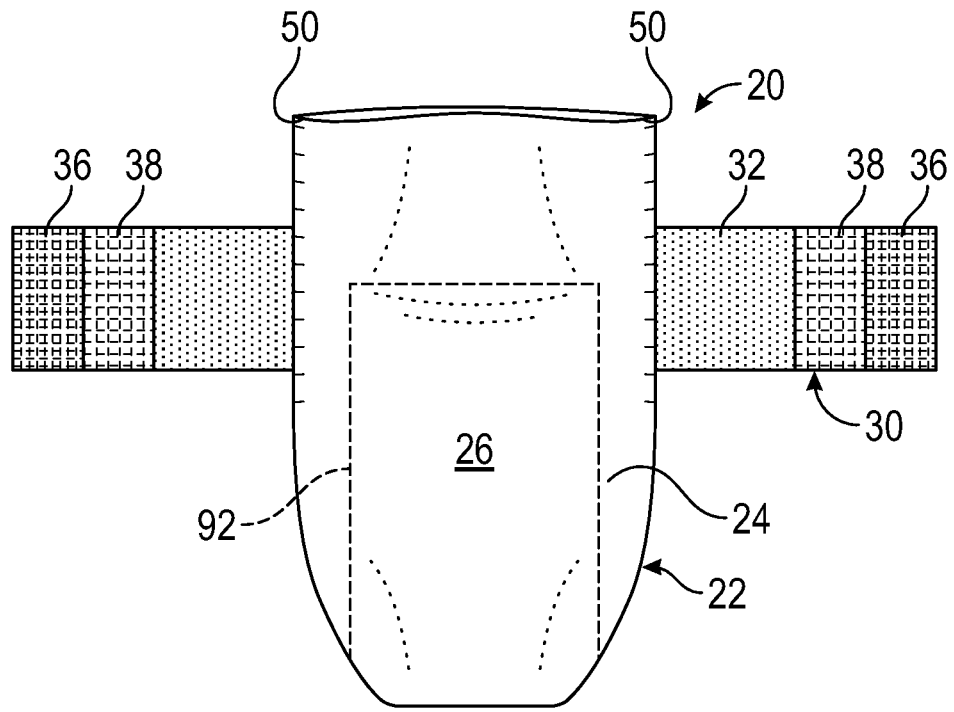
FIG. 1A is a front view of the hygienic article according to the principles of the present disclosure in a folded configuration and the fastening strap disengaged.
Figure 1B:
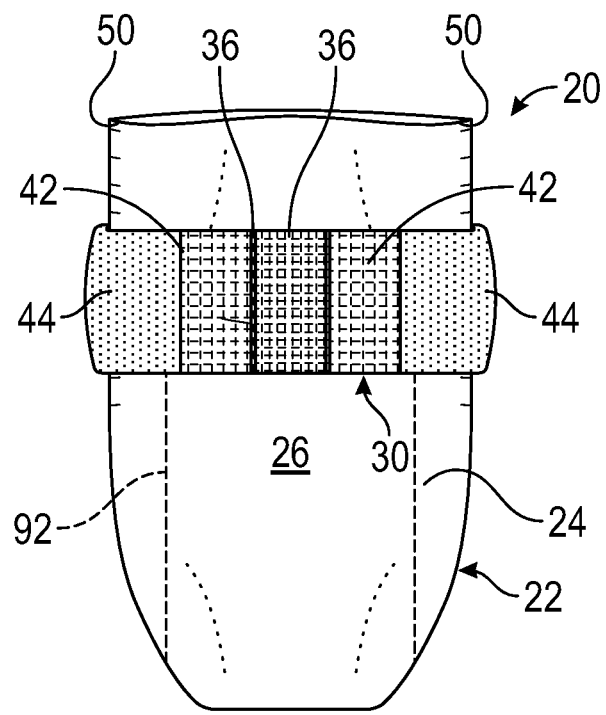
FIG. 1B is the view of FIG. 1A with the fastening strap engaged.
Figure 2:
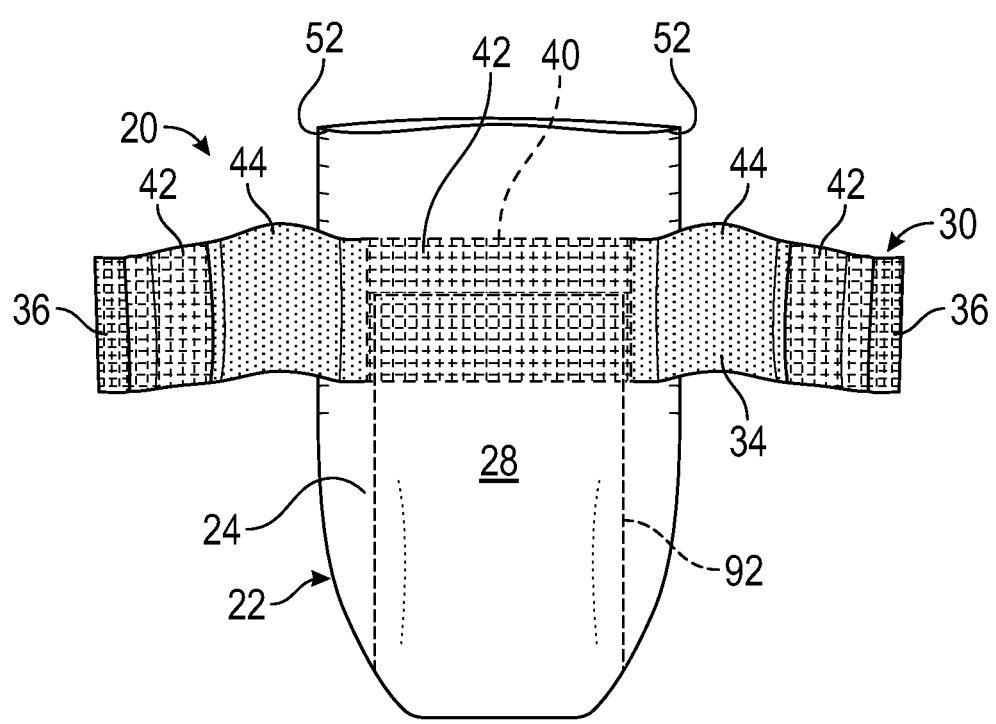
FIG. 2 is a back view of the article of FIG. 1A.

Referring to FIGS. 1A, 1B and 2, a hygienic article 20 according to the principles of the present disclosure includes a chassis 22 with a non-woven outer layer 24. In this exemplary folded configuration, chassis 22 has a front side 26 and a back side 28.

The hygienic article 20 includes a fastening strap 30 fixed to the chassis 22 at the back side 28. Fastening strap 30 is fixed to the chassis 22 at a central portion of the fastening strap 30. The inner surface 32 of the fastening strap 30 interfaces with the back side 28 of chassis 22, and the outer surface 34 of the fastening strap 30 is opposite the inner surface 32. Fastening strap 30 includes pull tabs 36 at opposing distal ends thereof and attachment material 38 on the inner surface 32 and proximate each of the pull tabs 36. Attachment material 38 is complementary to the non-woven outer layer 24 in that these materials releasably secured engagement. By example, the attachment material 38 may be include a hook material, and the outer layer 24 may include a loop material with which the hook material can engage and releasably secure.

Figure 6:
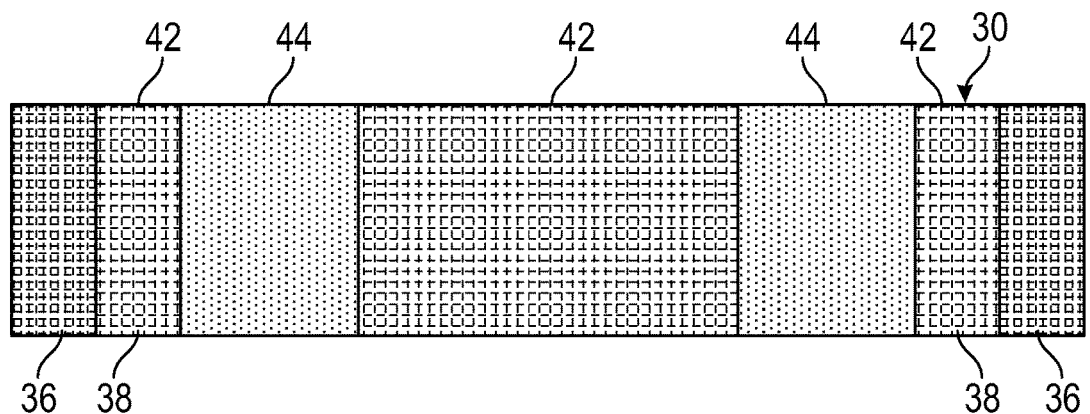
FIG. 6 is a top view of a fastening strap with stretch panels and hook attachments for a hygienic article according to the principles of the present disclosure.

With particular reference to FIG. 2, fastening strap 30 is secured to the chassis 22 across an attachment interface 40 between the chassis 22 and a central portion of the fastening strap 30. The central portion of the fastening strap 30 and distal portions of the fastening strap 30 include non-woven material. Between the non-woven material portions 42, fastening strap 30 includes elastic portions 44. In the exemplary embodiment illustrated in, e.g., FIG. 6, the fastening strap 30 has two elastic material portions 44 alternating between three non-woven material portions 42. It should be understood that other configurations of variable elasticity between central and distal portions of a fastening strap 30 are within the scope of the present disclosure.

In some embodiments of the present disclosure, attachment interface 40 extends substantially across the back side 28 of the chassis 22, and fastening strap 30 extends substantially equally from the back side 28. In such embodiments, tensile forces applied to the fastening strap 30 are born by the fastening strap 30 and are not transferred to a localized portion of the back side 28 of the chassis 22. Such a configuration provides stability and comfort to a user, by maintaining the position of the chassis 22 against the anatomy, while allowing the elastic material portions 44 of the fastening strap 30 and the elasticized side panels 58 of the chassis 22 to accommodate, e.g., changes in size and position of the anatomy and position of the user. Such a configuration also facilitates use of the hygienic article 20 by having equal portions of the fastening strap 30 on both sides of the hygienic article 20, which allows for securing of the article 20 without twisting and use of either hand as dominant.

The front side 26 of the chassis 22 provides a landing zone for the attachment material portions 38 of the fastening strap 30. In some embodiments, the fastening strap 30 may, in part, engage with itself—e.g. the non-woven material portions 42 on the outer surface 34 of the fastening strap 30 may also be complementary to the attachment material 38 and, thereby, further define a landing zone for the other end of the fastening strap 30.

In a folded configuration such as FIGS. 1A, 1B, and 2, chassis component 22 is folded over approximately halfway along the length thereof, with front corners 50 brought adjacent to back corners 52, with the non-woven outer layer 24 on the exterior, defining the front side 26 and the back side 28 of the chassis 22.

Figure 3:
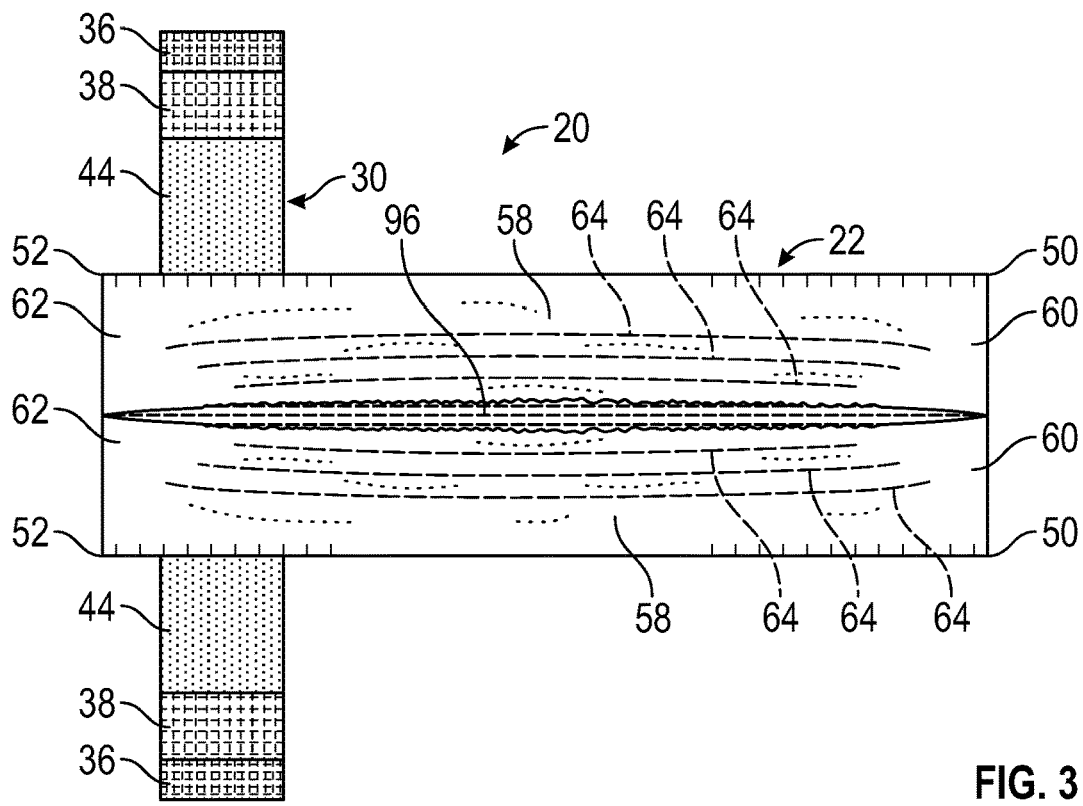
FIG. 3 is a top view of the article of FIG. 1A with the chassis of the article in an unfolded, stretched configuration.
Figure 4:
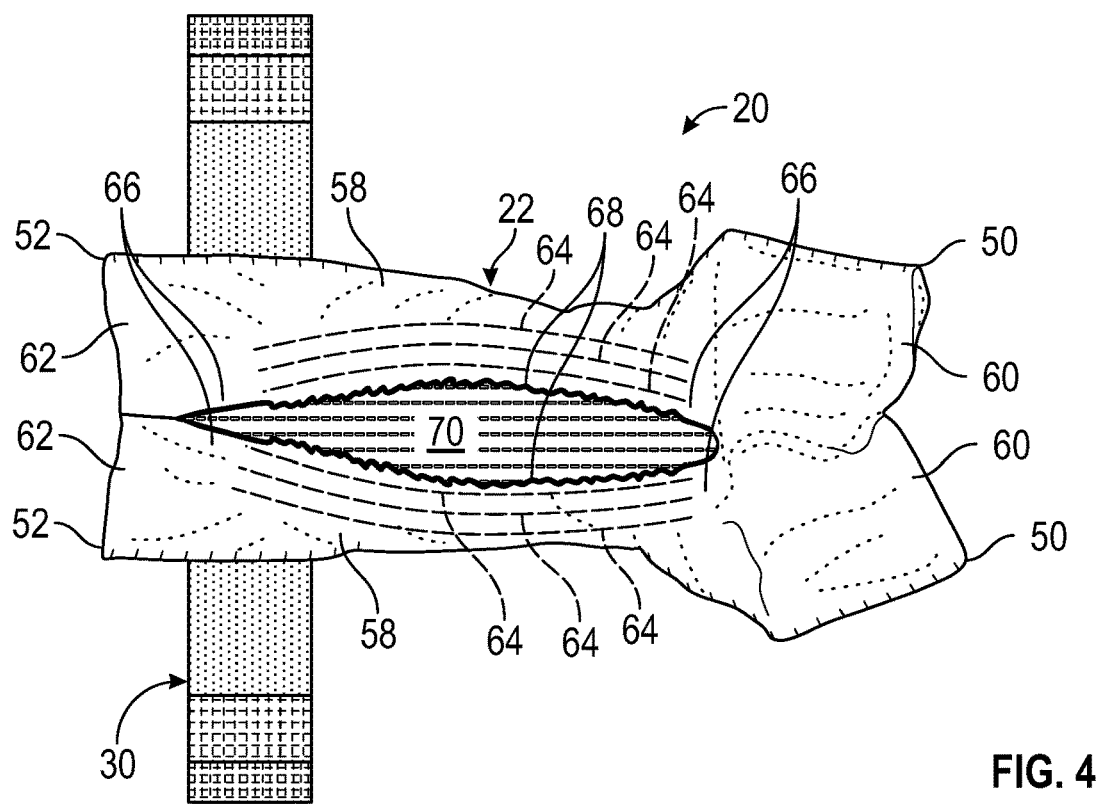
FIG. 4 is a perspective view of the article of FIG. 1A in a partially unfolded, relaxed configuration.
Figure 5:
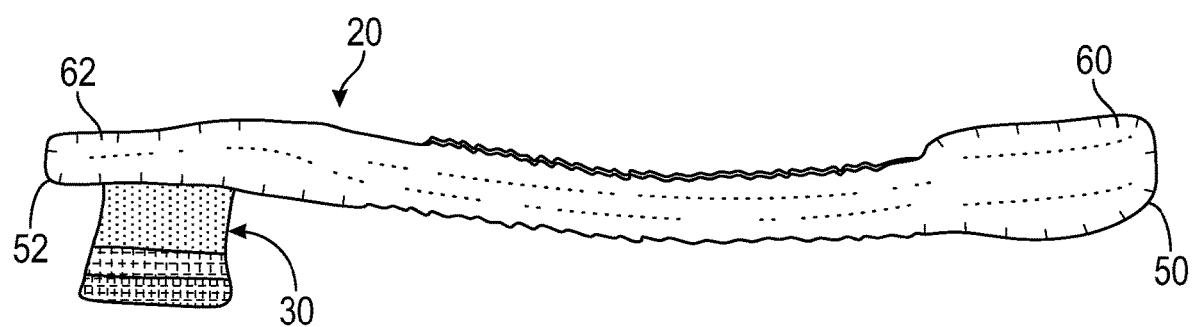
FIG. 5 is a side view of the article of FIG. 1A in the partially unfolded, relaxed configuration of FIG. 4.

With further reference to FIGS. 3 and 4, the hygienic article 20 includes two elasticized side panels 58. According to the principles of the present disclosure, the elasticized side-panels 58 provide radially inward forces against the anatomy of a user in the pouch 70 of the article 20. These forces contribute to securing article 20 to the user, while the elasticity allows article 20 to conform the article 20 to the anatomy of the user during use.

Side panels 58 include breathable, hydrophobic material. As illustrated in the example of FIG. 3, with the chassis 22 in an unfolded configuration, side panels 58 extend the length of chassis 22 between front corners 50 and back corners 52. Each of side panels 58 extends over substantially half of the surface of the unfolded chassis 22 and are each continuously coupled about the perimeter of chassis 22 on the three exterior sides thereof that overlap the perimeter of chassis 22. In some embodiments, side panels 58 are integral with the non-woven outer layer 24 and are secured to the chassis at distal ends 60 and 62, respectively, with, e.g., adhesive, ultrasonic bonds, pressure welds, or heat bonds. Side panels 58 are not engaged with each other at the midpoint of the chassis 22 along the length of the chassis 22. Each of the side panels 58 may include varied numbers of elastic threads 64 configured to pull the chassis 22 into a folded configuration with the respective front corners 50 and back corners 52 toward each other. With particular reference to the example illustrated in FIG. 4, according to the principles of the present disclosure, when the chassis 22 is folded, the side panels 58 define an opening to a pouch 70 defined between the interior surfaces of the side panels 58 and the chassis 22.

In some embodiments of the present disclosure, the outer layer 24 and the elasticized side-panels 58 are formed from a single sheet 80. As illustrated in the example of FIGS. 7A-B and FIGS. 8A-B, such sheet 80 may be configured to be initially approximately three times the width of the main chassis 22. The side panels 58 are defined from the sheet 80 by laterally folding the portions of sheet 80 outside of the chassis 22 in half at folds 82. In such embodiments, the side panels are two layers of the material of sheet 80, each half the width of the chassis 22, while the outer layer 24 of the chassis 22 is a single layer of the same sheet 80. With further reference to FIGS. 9A-B, the distal ends 60, 62 of the side panels 58 are secured to the chassis 22 with, e.g., adhesive. Thereby, the elasticized side panels 58 define a one-piece tubular shape defining a pouch therein to encapsulate the male anatomy. In some embodiments, the height of the side-panels is 40-50 mm and are variable depending upon the size change and specific fit needed for a user and the sizing of the other components of the article 20.

Side panels 58 include one or more elastic threads 64. As illustrated in the example in the Figures, side panels 58 each include three of elastic threads 64. In other embodiments of the elasticized side-panels 58, three to twelve elastic threads are used per side, strategically spaced for optimal gathering capability and encapsulated between layers of the sheet 80. In such embodiments, the threads are between 150 and 180 mm long and are spaced between 3 mm and 10 mm apart. These dimensions are variable to match the required size and fit and to correspond to the other components of the article.

The elastic threads 64 may be configured to provide variable elasticity, such as providing a center portion of the elasticized side-panels 58 between the distal ends 60, 62 with relatively greater elasticity and, thus, relatively relaxed elasticity at the ends 60, 62. According to the principles of the present disclosure, the elastic threads 64 may provide variable elasticity by varying the stretch factor applied to the threads 64 while the threads 64 are being affixed to the side panels 58. In some embodiments, different ones of the elastic threads 64 in a single side panel may be configured with varying stretch factor profiles.

In embodiments where the center portion of the side panels 58 has greater elasticity, the configuration facilitates use of the article 20, conformity to the penis, a secure fit to the penis and comfort during use. With the structure of the article 20 gathering the side panels 58 in the central portion thereof as the front corners 50 and back corners 52 are brought together, the pouch 70 is defined. Being gathered at the center, the elastic side panels 58 can accommodate variation in anatomy and positioning from front to back or back to front. Being elastic, the side panels 58 can engage around the male anatomy prior to being overlapped with the fastening strap 30, thereby allowing the compressive forces of the fastening strap 30 to also be applied to the side panels 58.

In some embodiments, the layers of the side panels 58 are secured with adhesive, ultrasonic bonds, pressure welds, or heat bonds at discrete locations along the length of the elastic threads 64 according to desired gathering properties of the non-woven material and, thereby, to provide the fit and function of the hygienic article 20 according to the principles of the present disclosure. In some embodiments, elastic snap back of the threads 64 is approximately 0.5 to 1.0 inch to localize gathering of the side-panels 58 at a center portion thereof. This distance is variable according to the desired size and fit and to correspond with the size of the other components of the hygienic article 20. The variable elasticity of the elasticized threads 64 in the side panels 58 allows the article 20 to accommodate variable changes in the shape and size of the penis, which may occur continually during use of the article 20.

In some exemplary embodiments, elastic threads 64 for the elasticized side-panels 58 may have a size of 680 decitex, and the threads 64 may be used at a stretch factor of between 1 to 3 times their relaxed length. It should be understood that the size of the threads 64 and the stretch factor applied to the threads 64 are variable according to the desired range of elasticity sought, size, and fit and to correspond with the size of the other components of the hygienic article 20. For example, the threads 64 can be in the range of 500-1100 decitex.

Referring to FIGS. 1A-B, 2, and 10A-B, the fastening strap 30 is secured to the back side 28 of the main chassis. When folded over and secured to the penis with the fastening strap 30 secured, the distal ends of the article 20 extend superiorly above the location of the fastening strap 30. This structure provides a consistent engagement between the user, the side panels 58, and the inner surface of the chassis 22. This structure also provides a path for air flow between the strap and the user through the breathable fabrics of the article 20, which further promotes comfort and simultaneously provides inhibition of skin irritation and skin deterioration by virtue of the enhanced air flow.

With the fastening strap 30 securing the article 20 to a user, the article 20 provides a secure and comfortable fit and accommodation of variable changes in penis size and position. With the elasticized components 44 of the fastening strap 30 providing compressive force to secure the chassis 22 to the anatomy, changes in size and position of the penis are accommodated and the penis is kept within the elasticized side panels 58—as opposed to the chassis shifting back and forth across a user between the pair of side panels 58. With the fastening strap 30 including elastic portions 44 overlapping the side panels 58, the strap 30 both anchors the chassis 22 and allows for the expansion of the side panels 58.

As illustrated in FIGS. 7A-B, 8A-B, 9A-B, and 10A-B, the chassis 22 of hygienic article 20 includes a plurality of layers. In the example of the Figures, the chassis 22 includes a non-woven, air permeable, moisture barrier back sheet 90 directly engaged with the portion of sheet 80 defining outer layer 24, the engagement being provided, in some embodiments, an adhesive layer 91. In such embodiments, the outer layer 24 of the chassis 22, as a soft outermost covering of the article 20, inhibits noise from the article 20 from adjustment or contact with clothing during movement of a user.

Adhered to the back sheet 90 on the inward side thereof is an absorbent core component 92, the core component extending across a smaller area of the chassis 22 than the back sheet 90. An acquisition distribution layer 94, being substantially equal to the core component 92 in the area of the footprint over the chassis 22, is layered on the core component 92 opposite the back sheet 90. A top sheet 96 overlaps the core component 92 and acquisition distribution layer 94. The top sheet 96 directly interfaces with the back sheet 90, and the top and back sheets 96, 90 are fixed with a window of adhesive that extends about and surrounds the core component 92 and the acquisition distribution layer 94. The top sheet 96 overlaps all edges of the back sheet 90, and, thus, the top sheet 96 and the side panels 58 define the pouch 70 therebetween and are the only components of the article 20 that may directly contact a user within the pouch 70.

In some embodiments, the core component 92 is fixed to the back sheet with adhesive. For example, the adhesive may be in the configuration of a narrow lengthwise strip 100 in the center of the chassis, to leave free as much of the surface area of the absorbent core component 92 as possible to receive and contain liquid. The core component 92 is selected to provide absorption of sporadic, partial leakage of bladder contents over time; in some embodiments, the article 20 provides substantially 2 ounces of liquid absorption capacity over time. To minimize the size and appearance of the article 20 while maximizing capacity, and because the article 20 is designed to support partial leakage over time, the core component 92 has a relatively high density as compared to conventional, larger incontinence articles. The size of the core component 92 and, in general, the article 20, not only minimizes the effect, if any, on the natural appearance undergarments of a user, but the contained size with substantially exposed surface area prevents pooling of leakage and the attendant discomfort and irritation of skin.

The non-woven back sheet 90 is an air permeable, moisture barrier material which functions to contain liquid drawn to the core component 90 within the article 20. With this structure, the article provides for airflow therein to, e.g., cool the contact area between the article and the user. By way of non-limiting example, the moisture barrier may include a poly-film material. In addition to or as an alternative to adhesive, the back sheet 90 may be, in some embodiments, secured to the core component by one of ultrasonic bonding, pressure welding, and heat bonding. In some embodiments in which the non-woven back sheet 90 is secured with adhesive, the adhesive is configured in a pattern, e.g. a dot matrix, the pattern being complementary to the configuration of one or both of the core component 92 and the non-woven back sheet 90, the pattern being complementary so as to secure the back sheet 90 while maximizing the absorption performance of the core component and minimizing the impediments to fluid flow in the article 20.

The absorbent core component 92, in some embodiments, includes a material made with absorbent polymers encapsulated within hydro-bonded cellulose sheets to provide maximum absorption with minimal thickness. Various levels of absorption can be achieved by different grades and patch sizes of such materials, e.g. from 0.5 fluid ounce to 6 fluid ounces. In some embodiments, the core component 92 is tenderized to make the article 20 more pliable and, thus, comfortable to a user. In some embodiments, width of the core component is 38 mm to 50 mm, and length is up to 170 mm. In accordance with the principles of the present disclosure, the dimensions of the core component may be varied to achieve desired absorption properties.

The acquisition distribution layer 94 is, in some embodiments, fixed to the core component 90 with a thin layer of adhesive 102. The thin layer of adhesive 102 avoids clogging of the through passages of the layer 94. The acquisition distribution layer 94 is a one-way moisture barrier material oriented to allow flow of liquid therethrough only to the core component but not from it; it allows fluid to pass through into the absorbent core component 92 and prevents backward flow of fluid by way of conical-shaped flow holes having a smaller end closest to and at the core component 92. In accordance with the principles of the present disclosure, this feature protects the comfort of the wearer by reducing the possible leaking of urine and soiling the clothing. In some embodiments of the article of the present disclosure, the one-way moisture barrier component 94 has a width of 40 mm to 60 mm and a length of 150 mm, which is variable in accordance with the size of the absorbent core component 92. In addition to or as an alternative to adhesive, the one-way moisture barrier component 94 may be secured to the core component by, e.g., one of ultrasonic bonding, pressure welding, and heat bonding, with the pattern of secured engagement of those components being of a design to not restrict the flow of urine or the one-way barrier characteristics of the conical shaped flow holes.

The hygienic article of the present disclosure includes a top sheet 96 interior and superior to the one-way moisture barrier 94. The top sheet 96 defines an inner surface of a pouch 70 of the article for direct contact with a user. The top sheet 96 may have an ultra-soft fiber configuration to provide a user comfort. The top sheet 96 is affixed to the back sheet 90 with a perimeter seal of adhesive within the footprint of the chassis 22, with the core component 94 and acquisition distribution layer 94 between the top and back sheets 96, 90. In some embodiments, the top and back sheets 96, 90 may be adhered with ultrasonic bonds, pressure welds, or heat bonds. The amount of adhesive, ultrasonic bonds, pressure welds, or heat bonds is limited to avoid rough or hard spots in the chassis 22 from the bond of the components that would irritate the skin of a user.

In some embodiments of the article of the present disclosure, the dimensions of the top sheet 96 are 55 mm wide by 180 mm long, which are variable in correspondence with the other components and to create different levels of size, fit, and absorption. The top sheet 96 material includes the properties of extreme softness and hydrophilic passages to allow urine to flow through unrestricted to the one-way moisture barrier component 94 and, in turn, into the absorbent core component 92. The assembly of the back sheet 90, absorbent core component 92, one-way moisture barrier component 94, and top sheet 96 comprises a chassis 22 of the article.

In some embodiments, the size of the fastening strap 30 is 140 mm long and between 12 mm and 30 mm wide, which dimensions are variable according to the desired size and fit and to correspond with the size of the other components of the hygienic article 20. In some embodiments according to the principles of the present disclosure, the fastening component may be in the form of a beading, band, strip, clamp, or belt to secure the hygienic article 20 to a user's anatomy while providing flexibility in performance and in adjustment of the fit of the article to the user. In some embodiments, the fastening component may be in the form of a beading of a skin-friendly silicone material. In some embodiments, the fastening component may include adjustable, pliable bands or band-strips. In some embodiments, the fastening component may include elasticized clamps that wrap around the proximal end of the article. In some embodiments, the fastening component is in the form of a reusable, relatively wire-like belt that is attached on the posterior center of the back of the chassis 22 and capable of being bent around the chassis 22 once the chassis 22 is in place on a user.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A hygienic article for a male comprising:
   an elongated chassis component including a moisture barrier back sheet, an absorbent core component, a one-way moisture barrier component coupled to the absorbent core component, and a top sheet overlapping the absorbent core component and the one-way moisture barrier component, the top sheet and the back sheet being affixed to each other with a seal therebetween, the seal extending about and surrounding the absorbent core component and the one-way moisture barrier component, with the moisture barrier back sheet being both air permeable and moisture impermeable;
   a single sheet defining an outer layer and variably elasticized side-panels, the outer layer of the single sheet being an outermost covering of the article, the variably elasticized side-panels of the single sheet extending from longitudinal sides of the chassis component, the side-panels having exterior corners folded over the chassis component to a lateral midpoint of the chassis component and coupled to the top sheet at opposing ends of the chassis component, the side-panels drawing the opposing ends of the chassis component to each other at a relaxed configuration of the side-panels, the side-panels and top sheet defining a pouch therebetween, the pouch being configured to receive a penis therein with the side-panels in a stretched configuration, the article being configured to surround the penis, provide adjustable compression from the side panels, and conform around the penis; and
   a fastening strap coupled to an exterior surface of the single sheet and spaced apart from one of the opposing ends of the chassis component, the fastening strap including an elasticized nonwoven material and hook material portions, the hook material portions configured to releasably secure to one or more landing zones on the single sheet of the chassis component with the elastic material of the fastening strap in a stretched configuration, the fastening strap being configured to extend around the article and provide adjustable compression in the stretched configuration to secure the penis within the pouch with the opposing ends of the chassis component and edges of the side panels extending partially outside of the fastening strap, with at least a portion of the elastic material of the fastening strap overlapping the side panels;

wherein the side-panels have a first elasticity in central portions thereof and a second elasticity at opposing ends thereof, the first elasticity being greater than the second elasticity configured to provide variable compression on the penis, with the fastening strap having zones of the elastic nonwoven material situated alternately between zones of non-elasticized non-woven material, and the article is configured to releasably secure to a user only on the penis and isolate the penis and leakage from the remainder of the user's body.

2. The hygienic article of claim 1, wherein the side-panels include one or more first elasticized threads each with a first thread elasticity and one or more second elasticized threads each with a second thread elasticity, the configuration of the one or more first elasticized threads and one or more second elasticized threads providing the side panels with the first elasticity in the central portions thereof and the second elasticity at opposing ends thereof.

3. The hygienic article of claim 1, wherein the side-panels include an elastic thread.

4. The hygienic article of claim 3, wherein each of the elastic thread is between 150 and 180 mm long.

5. The hygienic article of claim 1, wherein the side panels each include two or more elastic threads are spaced between 3 mm and 10 mm apart from each other.

6. The hygienic article of claim 1, wherein the one-way moisture barrier component is fixed to the absorbent core component with at least one of a thin layer of adhesive, ultrasonic bonds, pressure welds, and heat bonds.

7. The hygienic article of claim 1, wherein the seal of the chassis component includes at least one of adhesive, ultrasonic bonds, pressure welds, and heat bonds.

8. The hygienic article of claim 1, wherein the hook material portions of the fastening strap are configured to releasably secure to a landing zone on an exterior surface of the fastening strap.

9. The hygienic article of claim 8, wherein the landing zone includes a non-woven material.

10. A hygienic article for a male comprising:
an elongated chassis component including a moisture barrier back sheet, an absorbent core component having a smaller surface area than the moisture barrier back sheet, a one-way moisture barrier component coupled to the absorbent core component, and a top sheet overlapping the absorbent core component and the one-way moisture barrier component, the top sheet and the moisture barrier back sheet having a seal therebetween, the seal extending about and surrounding the absorbent core component and the one-way moisture barrier component, the moisture barrier back sheet is air permeable and moisture impermeable;
a single sheet defining an outer layer and elasticized side-panels, the outer layer of the single sheet being an outermost covering of the article, the elasticized side-panels of the single sheet extending from longitudinal sides of the chassis component, the side-panels having exterior corners folded over the chassis component and coupled to the top sheet at opposing ends of the chassis component, the side-panels drawing the opposing ends of the chassis component to each other at a relaxed configuration of the side-panels, the side-panels and top sheet defining a pouch configured to receive and encapsulate a user's penis therein with the side-panels in a stretched configuration; and
a flexible fastening component coupled to the single sheet, the flexible fastening component configured to extend around the chassis component and the side panels and releasably engage the single sheet, with opposing ends of the chassis component and edges of the side panels extending partially outside of the flexible fastening component to secure the user's penis directly within the pouch, the article being configured to releasably secured to the user only on the user's penis, the flexible fastening component and the side panels being configured to adjust and conform the hygienic article to a changing size and shape of a user's penis during use of the article.

11. The hygienic article of claim 10, wherein the flexible fastening component is in the form of a fastening strap coupled to the single sheet, the fastening strap being configured to include variable zones of elasticity situated alternately between zones of non-elasticized non-woven material, the fastening strap including hook material portions configured to releasably secure to the single sheet.

12. The hygienic article of claim 11, wherein the flexible fastening component further includes pull tabs.

13. The hygienic article of claim 10, wherein the absorbent core is fixed to the moisture barrier with at least one of adhesive, ultrasonic bonds, pressure welds, and heat bonds.

14. The hygienic article of claim 10, wherein the flexible fastening component is in the form of a belt component configured to bend around the chassis component.

15. A hygienic article for a male comprising:
an elongated chassis component including a moisture barrier back sheet, an absorbent core component, a one-way moisture barrier component coupled to the absorbent core component, and a top sheet overlapping the absorbent core component and the one-way moisture barrier component, the top sheet and the back sheet being affixed to each other with a seal therebetween, the seal extending about and surrounding the absorbent core component and the one-way moisture barrier component, the moisture barrier back sheet is air permeable and moisture impermeable;
a single sheet defining an outer layer and elasticized side-panels, the outer layer of the single sheet being an outermost covering of the article, the elasticized side-panels of the single sheet extending from longitudinal sides of the chassis component, the side-panels having exterior corners folded over the chassis component to a lateral midpoint of the chassis component and coupled to the top sheet at opposing ends of the chassis component, the side-panels drawing the opposing ends of the chassis component to each other at a relaxed configuration of the side-panels, the side-panels and top sheet defining a pouch therebetween, the pouch being configured to receive a penis therein with the side-panels in a stretched configuration, the article being configured to surround the penis, engage directly onto the penis, and conform around the penis upon the side panels being relaxed from the stretched configuration; and a fastening strap coupled at a middle portion to an exterior surface of the chassis component spaced apart from one of the opposing ends, the fastening strap including an elastic material and hook material portions at each of the ends, the hook material portions configured to releasably secure to at least one of the exterior surface of the chassis component and a portion of the strap outside of the hook material portions, each side of the fastening strap being configured to extend at least partially around the article and provide compression in the stretched configuration to secure the penis within the pouch with the opposing ends of the chassis component and edges of the side panels extending partially outside of the fastening strap opposite the pouch, at least a portion of the elastic material of each side of the fastening strap overlapping at least a portion of the side panels;

wherein the side-panels have a first elasticity in central portions thereof and a second elasticity at opposing ends thereof, the first elasticity being greater than the second elasticity, the fastening strap has zones of the elastic material situated alternately between zones of non-elasticized non-woven material, and the article is configured to releasably secure to a user only on the penis.

16. The hygienic article of claim 2, wherein the one or more first elasticized threads each with the first thread elasticity is sized with a different thickness than the one or more second elasticized threads each with the second thread elasticity.

17. The hygienic article of claim 5, wherein the two or more elastic threads includes one or more first elasticized threads each with a first thread elasticity and one or more second elasticized threads each with a second thread elasticity.

18. The hygienic article of claim 17, wherein the one or more first elasticized threads each with the first thread elasticity is sized with a different thickness than the one or more second elasticized threads each with the second thread elasticity.

* * * * *